United States Patent [19]

Huang et al.

[11] Patent Number: 4,465,679
[45] Date of Patent: Aug. 14, 1984

[54] 1,2-DIAZA-3-ONE COMPOUNDS, THEIR USE IN TREATING HYPERTENSION AND PHARMACEUTICAL COMPOSITIONS THEREOF

[75] Inventors: Fu-chih Huang, Boonton, N.J.; Howard Jones, Ossining; Wan-Kit Chan, Yorktown Heights, both of N.Y.

[73] Assignee: USV Pharmaceutical Corporation, Tarrytown, N.Y.

[21] Appl. No.: 462,643

[22] Filed: Jan. 31, 1983

[51] Int. Cl.³ .................. A61K 31/55; C07D 243/02
[52] U.S. Cl. ............................... 424/244; 424/250; 424/273 R; 260/239.3 R; 544/239; 544/240; 548/365
[58] Field of Search ............... 260/239.3 R; 544/239, 544/240; 548/365; 424/244, 250, 273 R

[56] References Cited

U.S. PATENT DOCUMENTS 4,409,146 10/1983 Thorsett et al. ............. 260/239.3 R Primary Examiner—Robert T. Bond

[57] ABSTRACT

Compounds of the formula

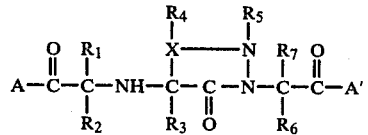

and their pharmaceutically-acceptable salts, wherein the substituents are as defined herein, having antihypertensive activity.

35 Claims, No Drawings

1,2-DIAZA-3-ONE COMPOUNDS, THEIR USE IN TREATING HYPERTENSION AND PHARMACEUTICAL COMPOSITIONS THEREOF

BACKGROUND OF THE INVENTION

This application relates to compounds, their pharmaceutically-acceptable salts, and pharmaceutical preparations made therefrom, having biological activity as inhibitors of the enzymatic conversion of angiotensin I to antiotensin II. The products comprising the present invention have utility in the treatment of hypertension in subjects suffering therefrom.

SUMMARY OF THE INVENTION

Broadly stated, the present invention comprises compounds of the formula

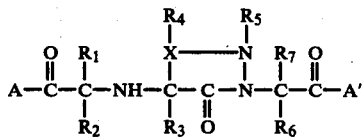

and their pharmaceutically-acceptable salts, wherein

X is a saturated chain of 1 to 5 carbon atoms;

A and A' are independently hydroxy, alkoxy, aryloxy, or hydroxyamino;

$R_1$, $R_2$, $R_3$, $R_4$, $R_6$ and $R_7$ are independently hydrogen, alkyl, alkenyl, alkynyl, aryl, aralkyl, fused cycloalkyl-aryl, fused aryl-cycloalkyl, fused cyclo-alkylarylalkyl, fused aryl-cycloalkyl-alkyl, aryloxyalkyl, arylalkyloxyalkyl, cycloalkyl, or cycloalkyl-alkyl, and $R_4$ can in addition be keto-oxygen or, when X contains at least 2 carbon atoms, $R_4$ can be an aryl ring or a cycloalkyl ring fused to X; and $R_5$ can be hydrogen, alkyl, alkenyl, alkynyl, acyl, cycloalkyl, cycloalkyl-alkyl, polycycloalkyl, polycycloalkyl-alkyl, aryl, aralkyl, polycyclic aryl, fused cycloalkylaryl, fused arylcycloalkyl, fused arylcycloalkyl-alkyl, or fused cycloalkylaryl-alkyl;

wherein the alkyl, alkoxy, alkenoxy, alkenyl, and alkynyl groups may carry substituents selected from the group consisting of hydroxy, acyloxy, aryl, alkoxy, aryloxy, amino, mono- or dialkylamino, acylamino, mercapto, mercaptoalkyl, and alkylthio; the cycloalkyl rings may include one or more hetero atoms, may be saturated or unsaturated, and may carry substituents selected from the group consisting of alkyl, hydroxy, alkylamino, and nitro; and the aryl rings may contain one or more hetero atoms and may carry substituents selected from the group consisting of carboxylic acid, cyano, carboxy-lower alkoxy, alkyl, hydroxy, alkoxy, hydroxyalkyl, halo, trifluoroalkyl, mercapto, alkylthio, mercaptoalkyl, amino, alkylamino, aminoalkyl, nitro, methylenedioxy, and sulfamyl;

wherein the alkyl groups contain 1 to 9 carbon atoms; and the cycloalkyl groups and the cycloalkyl portions of substituents containing cycloalkyl groups contain 3 to 9 carbon atoms.

DESCRIPTION OF THE PREFERRED EMBODIMENTS

Preferred compounds of the present invention are those of the general formula given above in which A and A' are each hydroxy or lower alkoxy; $R_1$, $R_2$, $R_3$, $R_6$ and $R_7$ are each hydrogen, alkyl, aryl, aralkyl, cycloalkyl, or w-amino alkyl wherein the amino is mono- or disubstituted with hydrogen, alkyl, aryl, or aralkyl, or is incorporated in a saturated or unsaturated one- or two-ring heterocyclic moiety containing preferably up to 12 atoms in the ring; and $R_4$ and $R_5$ are independently hydrogen, alkyl, aryl, cycloalkyl, or heteroaryl, any of which hydrocarbyl groups can be substituted or unsubstituted. Included as preferred groups are groups in which $R_5$ provides diuretic activity to the compound (1), e.g., sulfonamido-chloro-phenyl.

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiary-butyl, amyl, iso-amyl, hexyl, octyl, and the like. Preferably the alkyl groups are lower alkyl, which term shall refer to alkyl groups containing from 1 to 6 carbon atoms, straight-chained or branched.

The alkenyl and alkynyl groups and moieties can also be straight or branched-chained groups containing from 2 to 9, and preferably 2 to 6, carbon atoms. Such groups include vinyl, ethynyl, propenyl, isopropenyl, and the like.

The acyl groups include such groups as alkanoyl, aroyl, and aralkanoyl, wherein the alkyl and aryl moieties are as defined herein, as well as sulfonyl, sulfamoyl, carbamoyl, and the like, optionally containing an alkyl moiety with 1 to 9 and preferably 1 to 6 carbon atoms.

The preferred substituents on the above alkyl, alkenyl, alkynyl, and acyl groups include hydroxy, alkoxy, amino, alkylamino, dialkylamino, mercapto, alkylmercapto, and the like.

The cycloalkyl groups and moieties are saturated or unsaturated and preferably contain 3 to 9 carbon atoms. By "polycycloalkyl" is meant 2 or more fused cycloalkyl rings, having a total of up to 20 carbon atoms. The cycloalkyl, aryl, polycycloalkyl, and fused aryl-cycloalkyl structures can also contain one or more, preferably one or two, hetero atoms, i.e., a sulfur, oxygen, or nitrogen atom, thereby forming a hetero-ring.

Preferred cyclic and polycyclic ring structures, whether connected directly to the main molecule, connected by an intervening alkyl chain, or incorporated with X, as —X—, as

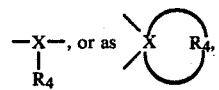

include such radicals as cyclopropyl, cyclobutyl, cyclopentyl, cyclohexyl, cycloheptyl, adamantyl, norbornyl, phenyl, tolyl, benzyl, phenethyl, indolyl, dimethoxyphenyl, hydroxybenzyl, indanyl, naphthyl, tetrahydronaphthyl, decanhydronaphthyl, pyridyl, quinolyl, guanidino, pyrrolidyl, pyrrolyl, morpholinyl, furyl, furfuryl, tetrahydrofurfuryl, benzimidazolyl, thienyl, imidazolyl, and the like. Preferred substituents on the ring structures i.e. aryl, cycloalkyl, polycyclic aryl, fused arylcycloalkyl, and polycycloalkyl ring structures whether or not containing a hetero atom, include hydroxy, alkyl, alkoxy, aryl, aryloxy, aralkyl, alkylamino, dialkylamino, alkenyl, alkynyl, carboxy, carboalkoxy, cyano, mercapto, amino, alkylmercapto, halo, trifluoromethyl, sulfonamide, and the like.

The halo groups include fluoro, chloro, bromo and iodo. Preferred hetero atoms are S, O, and N.

Substituents which are "unsaturated" contain one or more double or triple bond.

Preferred compounds are those in which at least one, and more preferably at least two, of $R_2$, $R_3$, $R_6$ and $R_7$ are hydrogen.

Compounds in accordance with the present invention are readily prepared employing known starting materials and procedures. It will be understood by those skilled in the art that the carbons to which $R_1$, $R_3$ and $R_6$ are attached can be asymmetric centers, such that the inventive compounds may exist in any of eight forms. Individual isomers and diastereoisomeric mixtures of said forms are within the scope of the invention. The preferred forms have (S,S,S) configuration.

The compounds of the formula (1) can be prepared by reacting a compound of the formula (2):

$$\text{(2)}$$

with compound (3):

$$\text{(3)}$$

wherein $R_3$, $R_4$, $R_5$, $R_6$, $R_7$, X and A' are as defined hereinabove, except that where $R_5$ is to be hydrogen in the final product the $R_5$ in compounds (3), (4), (5), (6), (7) and (10) should be instead a $$-\overset{O}{\underset{\|}{C}}OY$$

group wherein Y is a lower alkyl group and preferably tertiary butyl; the reaction of compound (10) with acid converts the —COOY group to —H. CBZ signifies carbonylbenzyloxy, i.e.

$$-\overset{O}{\underset{\|}{C}}-O-CH_2-\text{C}_6\text{H}_5$$

The product of reacting compounds (2) and (3), which is compound (4), $$\text{(4)}$$

is reacted with hydrogen over palladium on charcoal in, e.g., ethanol to form compound (5):

$$\text{(5)}$$

Compound (5) is reacted with DCC (dicyclohexylcarbodiimide) to compound (6):

$$\text{(6)}$$

which is then reacted with hydrazine to form compound (7)

$$\text{(7)}$$

To form compounds in which $R_2$ is hydrogen, compound (7) is reacted under reductive conditions with a compound of the formula (8)

$$R_1-\overset{O}{\underset{\|}{C}}-\overset{O}{\underset{\|}{C}}-A \quad \text{(8)}$$

Otherwise, a compound of formula (9)

$$R_1-\overset{L}{\underset{R_2}{\overset{|}{C}}}-\overset{O}{\underset{\|}{C}}-A \quad \text{(9)}$$

is reacted with compound (7) wherein L is a leaving group such as chloro or bromo.

In compounds (8) and (9) $R_1$ and A have the meaning set forth hereinabove. The product of reacting compound (7) with compound (8) or (9) is compound (10)

$$\text{(10)}$$

which is reacted with e.g. HCl in solution to form compounds having formula (1).

Each of the above reactions proceeds in a straightforward manner in a suitable solvent at temperatures ranging from 0° C. to 150° C.

The products are obtained typically as a mixture of diasteroisomers which can be separated by standard methods of fractional crystallization or chromatography.

The compounds of this invention form acid salts with various inorganic and organic acids which are also within the scope of the invention. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin-to-angiotensin I-to-angiotensin II sequence by inhibiting angiotensin I converting enzyme and reducing or eliminating the formation of the pressor substance angiotensin II and therefore are useful in reducing or relieving hypertension. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE 1

To a solution of N-t-butoxycarbonyl-N'-benzyloxycarbonyl-N'-(t-butylacetate)hydrazine (3.8 g) in 10 ml of DMF is added sodium hydride (470 mg), and then a solution of benzyl-5-bromo-2-(phthalimido)pentanoate (5.86 g in 10 ml DMF) is added dropwise in 10 min. The reaction mixture is stirred at 100° C. for 5 hours. After concentration in vacuo, the residue is taken up into ethyl acetate, washed with water, dried and evaporated to dryness. Purification by dry column chromatography gives 5.2 g of product (I-A), benzyl 2-phthalimido-5-[N-t-butoxycarbonyl-N'-benzyloxy-carbonyl-N'-(t-butylacetate)hydrazino]pentanoate:

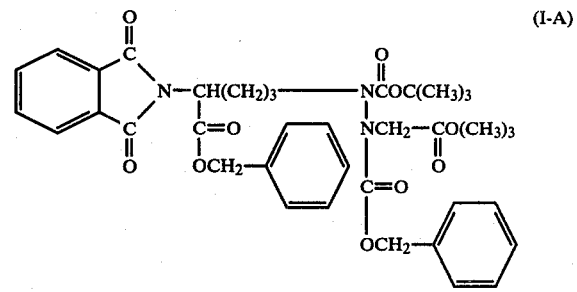

A solution of 3 g of product (I-A) and 300 mg of 5% Pd-C in 50 ml of ethanol is hydrogenated at 40 psi for 4 hours. The reaction mixture is filtered and concentrated to give 2 g of product (I-B), 2-(phthalimido)-5-[(N-t-butoxycarbonyl)-N'-(t-butyl acetate)hydrazino]pentanoic acid:

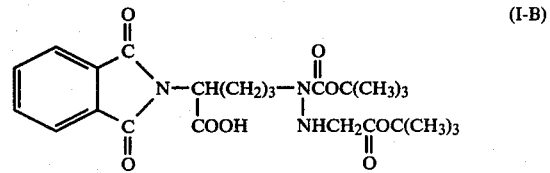

A mixture of product (I-B) (2.5 g) and DCC (1.1 g) in 30 ml of ethylenedichloride is stirred at room temperature overnight. After filtration, the organic solution is washed with HCl, saturated NaHCO₃, and water, and dried. The organic solution is concentrated and the residue purified by dry column chromatography to give 1.4 g of product (I-C), 1-t-butoxy-carbonyl-2-(t-butyl acetate)-4-(phthalimido)-1,2-diazapin-3-one:

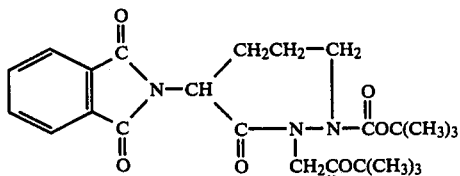
(I-C)

A solution of 1 g of product (I-C) and 108 mg of 50% hydrazine-hydrate in 10 ml of dioxane was warmed up to 50° C. for 1 hour. The reaction mixture is concentrated and the residue purified by dry column chromatography to give 650 mg of product (I-D), 4-Amino-1-t-butoxycarbonyl-2-(t-butyl-acetate)-1,2-diazapin-3-one:

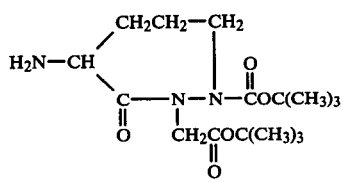
(I-D)

A mixture of 600 mg of product (I-D), ethyl 2-keto-4-phenyl butyrate (2 g), and sodium cyanoborohydride (100 mg) in 10 ml of ethanol is stirred at room temperature overnight. After filtration, organic solvent is concentrated and the residue is treated with 1N HCl solution to decompose excess hydride. The reaction mixture is neutralized and then extracted with ethyl acetate. The organic solution is washed with water, dried, concentrated and the crude product is purified by dry column chromatography to give 0.5 g of product (I-E), 1-t-butoxycarbonyl-2-(t-butyl-acetate)-4-(1-carbethoxy-3-phenylpropyl-1-amino)-1,2-diazapin-3-one:

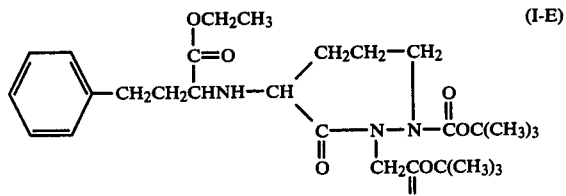
(I-E)

0.5 g of product (I-E) in 10 ml of ether is treated with anhydrous HCl in ether at 0° C. for 3 hours. The organic solution is concentrated to give 400 mg of product (I-F), 4-(1-carbethoxy-3-phenylpropyl-1-amino)-1,2-diazapin-3-one-2-acetic acid:

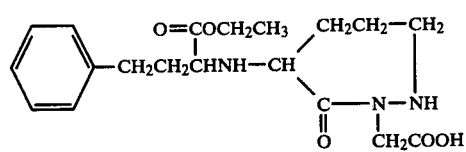
(I-F)

The following compounds are made in a manner wholly analogous to that shown above for compound (I-F):

EXAMPLE 2

4-(1-Carbethoxy-3-phenylpropyl-1-amino)-1-phenyl-1,2-diazapin-3-one-2-acetic acid

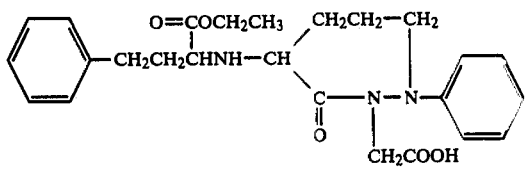

EXAMPLE 3

4-(1-Carbethoxy-3-phenylpropyl-1-amino)-1-ethyl-1,2-diazapin-3-one-2-acetic acid

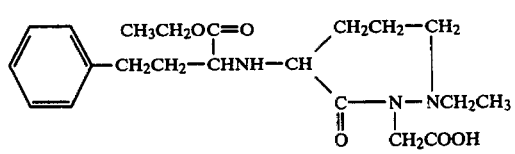

EXAMPLE 4

4-(1-Carbethoxy-ethyl-1-amino)-1,2-diazapin-3-one-2-acetic acid

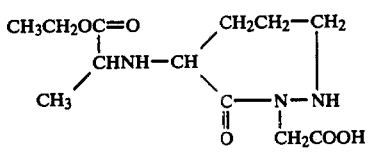

EXAMPLE 5

4-(1-Carbethoxy-4-aminobutyl-1-amino)-1,2-diazapin-3-one-2-acetic acid

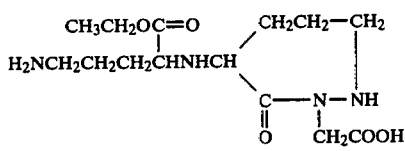

EXAMPLE 6

4-(1-Carbethoxy-3-phenylpropyl-1-amino)-hexahydropyridazine-3-one-2-acetic acid

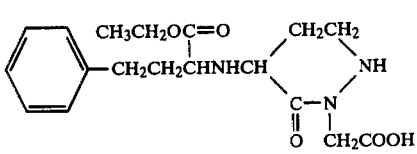

EXAMPLE 7

4-(1-Carbethoxy-3-phenylpropyl-1-amino)-1,2-diazocine-3-one-2-acetic acid

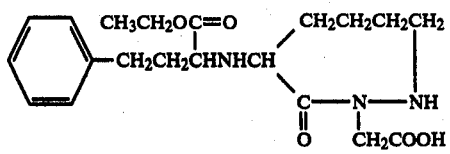

What is claimed is:

1. A compound of the formula

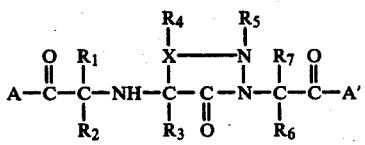

and its pharmaceutically-acceptable acid addition salts, wherein

X is a saturated chain of 1 to 5 carbon atoms;

A and A' are independently hydroxy, alkoxy, phenoxy, or hydroxyamino;

$R_1$, $R_2$, $R_3$, $R_4$, $R_6$ and $R_7$ are independently hydrogen, alkyl, alkenyl, alkynyl, phenyl, phenylalkyl, fused cycloalkyl-phenyl, fused phenyl-cycloalkyl, fused cycloalkylphenyl-alkyl, fused phenyl-cycloalkyl-alkyl, phenoxyalkyl, phenylalkyloxyalkyl, cycloalkyl, or cycloalkyl-alkyl, and $R_4$ can in addition be keto-oxygen or, when X contains at least 2 carbon atoms, $R_4$ can be a phenyl ring fused to 2 consecutive atoms of X or a cycloalkyl ring fused to X; and $R_5$ can be hydrogen, alkyl, alkenyl, alkynyl, alkanoyl, benzoyl, phenyl-alkanoyl, carbamoyl, cycloalkyl, cycloalkyl-alkyl, polycycloalkyl, polycycloalkyl-alkyl, phenyl, phenylalkyl, polyphenyl, fused cycloalkyl-phenyl, fused phenyl-cycloalkyl, fused phenyl-cyclo-alkyl-alkyl, or fused cycloalkyl-phenyl-alkyl;

wherein the alkyl, alkoxy, alkenoxy, alkenyl, and alkynyl groups can carry one or more substituents selected from the group consisting of hydroxy, alkanoyloxy, benzoyloxy, phenylalkanoyl, carbamoyl, phenyl, alkoxy, phenoxy, amino, mono- or dialkyl-amino, alkanoylamino, benzoylamino, mercapto, mercaptoalkyl, and alkylthio; the cycloalkyl rings can carry one or more substituents selected from the group consisting of alkyl, hydroxy, alkylamino, and nitro; and the phenyl rings can carry one or more substituents selected from the group consisting of carboxylic acid, cyano, carboxy-lower alkoxy, alkyl, hydroxy, alkoxy, hydroxyalkyl, halo, trifluoroalkyl, mercapto, alkylthio, mercaptoalkyl, amino, alkylamino, aminoalkyl, nitro, methylenedioxy, and sulfamyl;

wherein the alkyl groups and moieties contain 1 to 9 carbon atoms; the alkenyl and alkynyl groups and moieties contain 2 to 9 carbon atoms; the polycycloalkyl groups have up to 20 carbon atoms; and the cycloalkyl groups and the cycloalkyl portions of substituents containing cycloalkyl groups contain 3 to 9 carbon atoms.

2. A compound or salt of claim 1 having an (S,S,S) structural configuration.

3. A compound of the formula:

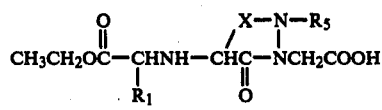

wherein

X represents a chain of from 1 to 5 unsubstituted methylene groups;

$R_1$ represents an alkyl group containing 1 to 6 carbon atoms, phenyl, phenylalkyl wherein the alkyl group contains from 1 to 6 carbon atoms, or alkylamine wherein the alkyl group contains from 1 to 6 carbon atoms; and $R_5$ represents hydrogen, alkyl containing 1 to 6 carbon atoms, phenyl, or phenylalkyl wherein the alkyl group contains 1 to 6 carbon atoms.

4. A compound or salt of claim 3 having an (S,S,S) structural configuration.

5. The compound according to claim 3 which is 4-(1-carbethoxy-3-phenylpropyl-1-amino)-1,2-diazapin-3-one-2-acetic acid.

6. The compound according to claim 3 which is 4-(1-carbethoxy-3-phenylpropyl-1-amino)-1-phenyl-1,2-diazapin-3-one-2-acetic acid.

7. The compound according to claim 3 which is 4-(1-carbethoxy-3-phenylpropyl-1-amino)-1-ethyl-1,2-diazapin-3-one-2-acetic acid.

8. The compound according to claim 3 which is 4-(1-carbethoxy-ethyl-1-amino)-1,2-diazapin-3-one-2-acetic acid.

9. The compound according to claim 3 which is 4-(1-carbethoxy-4-aminobutyl-1-amino)-1,2-diazapin-3-one-2-acetic acid.

10. The compound according to claim 3 which is 4-(1-carbethoxy-3-phenylpropyl-1-amino)-hexahydropyridazine-3-one-2-acetic acid.

11. The compound according to claim 3 which is 4-(1-carbethoxy-3-phenylpropyl-1-amino)-1,2-diazocine-3-one-2-acetic acid.

12. A pharmaceutically-acceptable acid salt of a compound according to claim 3 wherein the acid is selected from the group consisting of hydrochloric, hydrobromic, sulfuric, nitric, acetic, fumaric, malic, maleic and citric acids.

13. A pharmaceutically-acceptable acid salt of a compound according to claim 5 wherein the acid is selected from the group consisting of hydrochloric, hydrobromic, sulfuric, nitric, acetic, fumaric, malic, maleic and citric acids.

14. A pharmaceutically-acceptable acid salt of a compound according to claim 6 wherein the acid is selected from the group consisting of hydrochloric, hydrobromic, sulfuric, nitric, acetic, fumaric, malic, maleic and citric acids.

15. A pharmaceutically-acceptable acid salt of a compound according to claim 7 wherein the acid is selected from the group consisting of hydrochloric, hydrobromic, sulfuric, nitric, acetic, fumaric, malic, maleic and citric acids.

16. A pharmaceutically-acceptable acid salt of a compound according to claim 8 wherein the acid is selected from the group consisting of hydrochloric, hydrobromic, sulfuric, nitric, acetic, fumaric, malic, maleic and citric acids.

17. A pharmaceutically-acceptable acid salt of a compound according to claim 9 wherein the acid is selected from the group consisting of hydrochloric, hydrobromic, sulfuric, nitric, acetic, fumaric, malic, maleic and citric acids.

18. A pharmaceutically-acceptable acid salt of a compound according to claim 10 wherein the acid is selected from the group consisting of hydrochloric, hydrobromic, sulfuric, nitric, acetic, fumaric, malic, maleic and citric acids.

19. A pharmaceutically-acceptable acid salt of a compound according to claim 11 wherein the acid is selected from the group consisting of hydrochloric, hydrobromic, sulfuric, nitric, acetic, fumaric, malic, maleic and citric acids.

20. The method of alleviating hypertension in a host suffering therefrom comprising administering to said host an antihypertensive effect amount of a salt of claim 12.

21. The method of alleviating hypertension in a host suffering therefrom comprising administering to said host an antihypertensive effect amount of a salt of claim 13.

22. The method of alleviating hypertension in a host suffering therefrom comprising administering to said host an antihypertensive effect amount of a salt of claim 14.

23. The method of alleviating hypertension in a host suffering therefrom comprising administering to said host an antihypertensive effect amount of a salt of claim 15.

24. The method of alleviating hypertension in a host suffering therefrom comprising administering to said host an antihypertensive effect amount of a salt of claim 16.

25. The method of alleviating hypertension in a host suffering therefrom comprising administering to said host an antihypertensive effect amount of a salt of claim 17.

26. The method of alleviating hypertension in a host suffering therefrom comprising administering to said host an antihypertensive effect amount of a salt of claim 18.

27. The method of alleviating hypertension in a host suffering therefrom comprising administering to said host an antihypertensive effect amount of a salt of claim 19.

28. An antihypertensive pharmaceutical preparation comprising about 0.1 to about 500 milligrams of a compound according to claim 3 in association with a pharmaceutically-acceptable carrier.

29. An antihypertensive pharmaceutical preparation comprising about 0.1 to about 500 milligrams of a compound according to claim 5 in association with a pharmaceutically-acceptable carrier.

30. An antihypertensive pharmaceutical preparation comprising about 0.1 to about 500 milligrams of a compound according to claim 6 in association with a pharmaceutically-acceptable carrier.

31. An antihypertensive pharmaceutical preparation comprising about 0.1 to about 500 milligrams of a compound according to claim 7 in association with a pharmaceutically-acceptable carrier.

32. An antihypertensive pharmaceutical preparation comprising about 0.1 to about 500 milligrams of a compound according to claim 8 in association with a pharmaceutically-acceptable carrier.

33. An antihypertensive pharmaceutical preparation comprising about 0.1 to about 500 milligrams of a compound according to claim 9 in association with a pharmaceutically-acceptable carrier.

34. An antihypertensive pharmaceutical preparation comprising about 0.1 to about 500 milligrams of a compound according to claim 10 in association with a pharmaceutically-acceptable carrier.

35. An antihypertensive pharmaceutical preparation comprising about 0.1 to about 500 milligrams of a compound according to claim 11 in association with a pharmaceutically-acceptable carrier.

* * * * *